United States Patent
Wang et al.

(10) Patent No.: US 10,215,689 B2
(45) Date of Patent: Feb. 26, 2019

(54) METHODS AND APPARATUS FOR ON-CHIP DERIVATIVE SPECTROSCOPY

(71) Applicant: Hong Kong Applied Science and Technology Research Institute Company Limited, Hong Kong (HK)

(72) Inventors: Jiaqi Wang, Hong Kong (HK); Chun Zhang, Hong Kong (HK); Wei Mong Tsang, Hong Kong (HK)

(73) Assignee: Hong Kong Applied Science and Technoloy Research Institute Company Limited, Hong Kong (HK)

( * ) Notice: Subject to any disclaimer, the term of this patent is extended or adjusted under 35 U.S.C. 154(b) by 94 days.

(21) Appl. No.: 15/874,956

(22) Filed: Jan. 19, 2018

(65) Prior Publication Data
US 2018/0209899 A1    Jul. 26, 2018

Related U.S. Application Data

(60) Provisional application No. 62/450,889, filed on Jan. 26, 2017.

(51) Int. Cl.
*G01N 21/25* (2006.01)
*G01J 3/433* (2006.01)

(52) U.S. Cl.
CPC ............ *G01N 21/255* (2013.01); *G01J 3/433* (2013.01)

(58) Field of Classification Search
CPC ............. G01J 3/42; G01J 3/433; G01N 21/27
See application file for complete search history.

(56) References Cited

U.S. PATENT DOCUMENTS 6,330,388 B1 *  12/2001  Bendett ............ C03C 4/00
                                                    385/132
9,046,481 B2     6/2015  Edler et al.
(Continued)

FOREIGN PATENT DOCUMENTS

CN         102680454 A       9/2012
CN         103424369 A      12/2013
(Continued)

OTHER PUBLICATIONS

International Search Report and Written Opinion of PCT application No. PCT/CN2018/073381 issued from the International Search Authority dated Apr. 17, 2018.
(Continued)

*Primary Examiner* — Maurice Smith
(74) *Attorney, Agent, or Firm* — Spruson & Ferguson (Hong Kong) Limited (57) ABSTRACT

A derivative spectroscopy system for achieving a tunable resolution of 2 nm or less in resolving spectral components of an input optical signal is provided so as to estimate derivative spectra of the input optical signal based on the resolved spectral components. In the system, a first dispersive-element structure spectrally decomposes the input optical signal into subband signals. A second dispersive-element structure receives part or all of the subband signals and spectrally decomposes the received subband signals to plural spectral components. A material having a temperature-variant refractive index is used to build the second dispersive-element structure, enabling a shift of center wavelength of each spectral component as small as 2 nm of less upon changing a temperature of the second dispersive-element structure. By obtaining three spectral-component sets obtained at three different predetermined temperatures with the center-wavelength shift of 2 nm or less, first- and
(Continued)

second-order derivative spectra are obtained with good accuracy.

20 Claims, 8 Drawing Sheets

(56) References Cited

U.S. PATENT DOCUMENTS

| | | | |
|---|---|---|---|
| 9,500,827 | B2 | 11/2016 | Hutchison et al. |
| 2004/0033004 | A1* | 2/2004 | Welch .................... B82Y 20/00 |
| | | | 385/14 |
| 2004/0223696 | A1 | 11/2004 | Berolo |
| 2006/0164639 | A1 | 7/2006 | Horn |
| 2007/0152154 | A1* | 7/2007 | DeCamp ............... G01J 3/2803 |
| | | | 250/339.07 |
| 2014/0085632 | A1 | 3/2014 | Preston |

FOREIGN PATENT DOCUMENTS

| | | |
|---|---|---|
| CN | 103604501 A | 2/2014 |
| WO | 83/00065 A1 | 1/1983 |
| WO | 03/102520 A1 | 12/2003 |

OTHER PUBLICATIONS

Tsalamanis et al.; Experimental demonstration of cascaded AWG access network featuring bi-directional transmission and polarization multiplexing; Optics Express; Mar. 8, 2004; vol. 12, Issue 5; Optical Society of America.

* cited by examiner

METHODS AND APPARATUS FOR ON-CHIP DERIVATIVE SPECTROSCOPY

CROSS-REFERENCE TO RELATED APPLICATION

This application claims the benefit of U.S. Provisional Patent Application No. 62/450,889, filed on Jan. 26, 2017, the disclosure of which is incorporated by reference herein in its entirety.

FIELD OF THE INVENTION

The present invention generally relates to chemical and biological sensors using derivative spectroscopy, and more particularly relates to compact on-chip integrated circuit derivative spectroscopy methods and apparatus.

BACKGROUND

In the area of portable devices that can efficiently and reliably identify chemical and biological agents, on-chip spectrometers provide an advantageous solution. A compact on-chip spectrometer can be realized in different configurations such as resonant wavelength filters like micro-ring resonators or Mach-Zender interferometers and dispersive components like echelle gratings, etched diffraction gratings, and arrayed-waveguide gratings (AWGs). AWG fabrication and device design have been steadily improving as AWGs are used in wavelength-division multiplexing for optical communication applications as well as on-chip spectrometer sensor applications. AWG designs with different materials and working wavelengths have been made for covering a wide spectral range for spectroscopy measurement.

However, one of the challenges in spectroscopic technologies is that the absorption spectrum of a real chemical system usually contains multiple wide and closely located bands of various compounds. Therefore, the total spectral curve is rather complex and broad, and some chemical components may only be partially and weakly shown in the spectra where the spectral resolution is insufficient for achieving a better spectral resolution (e.g., ≤2 nm).

Derivative spectroscopy measures the low intensity bands overlapped by bands of higher intensity in the absorption spectra by utilizing the derivatives of the absorption spectrum data for qualitative and quantification analysis. In the last several decades, derivative spectroscopy has had increased practical applications because the fast development of microcomputers has enabled the easy and fast generation of high sensitivity, high resolution and low noise high-order derivative spectra.

Figure 1A:
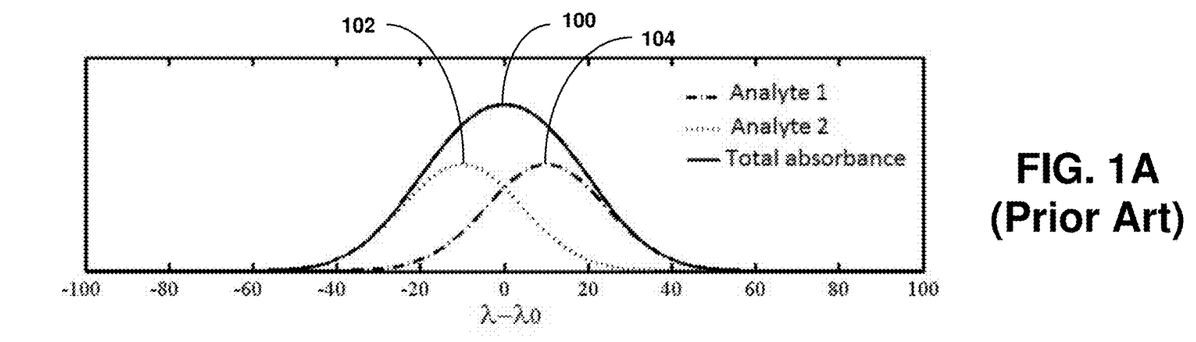

According to the Beer-Lambert law, the light absorbed by a layer of substance is described by $$I = I_0 \times 10^{-\varepsilon C d} \quad (1)$$

where $I_0$ and $I$ are input and transmitted optical intensities, respectively, $\varepsilon$ is a wavelength dependent coefficient, C is a concentration of a substance and d is a thickness of the substance layer. Absorbance is defined as $$A = \log_{10}(I_0/I) \quad (2)$$

and the absorbance as a function of wavelength $\lambda$, denoted as $$A = f(\lambda), \quad (3)$$

can be approximated by various types of functions, such as Gaussian equation and Lorentzian equation. However, as said before, a challenge in spectroscopic technologies is that the absorption spectrum of a real chemical system usually contains multiple wide and closely located bands of various compounds and each form of the absorption band may vary from known functions. Therefore, the total spectral curve is rather complex, and some components may be only partially or weakly displayed. One such spectral curve 100 is depicted in FIG. 1A where two closely located absorption bands 102, 104 cannot be resolved in the total absorption curve 100.

Figure 1B:
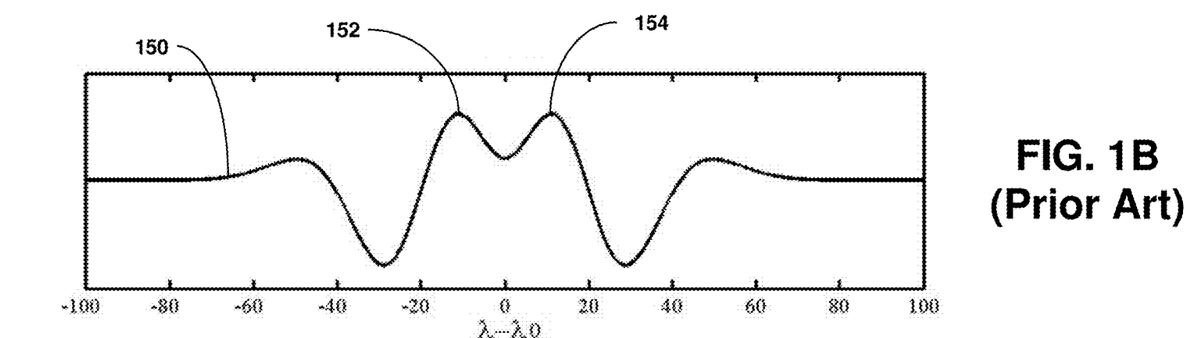
Figure 2:
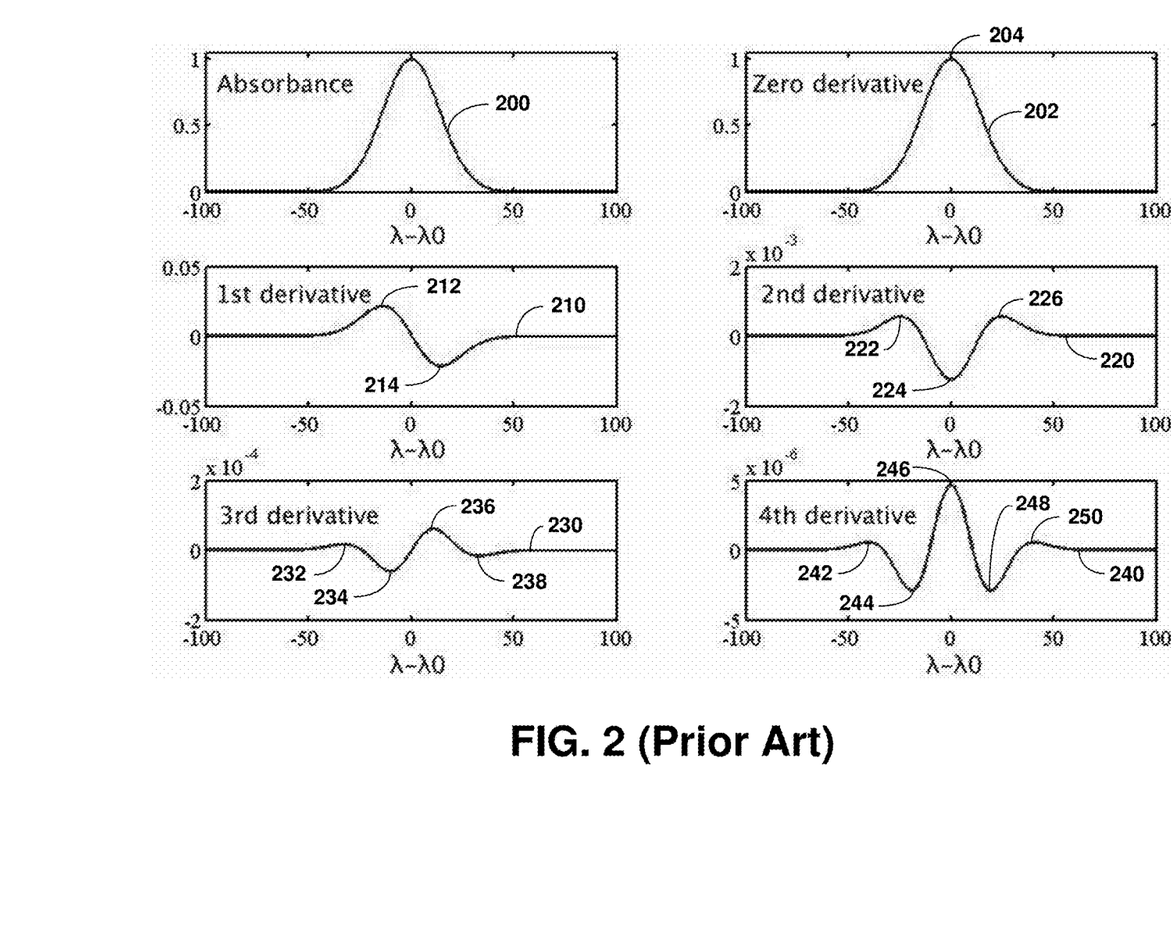
FIG. 2 depicts a typical Gaussian absorbance spectrum and its derivative spectra.

Derivative spectroscopy provides a powerful tool to solve such problems mentioned. Firstly, considering a single absorption band with a Gaussian curve shape 200, the Nth order derivative spectrum has N+1 bands, as shown in FIG. 2 (where the zeroth-derivative spectrum 202, i.e. the original Gaussian spectrum 200, has one band 204, the first derivative spectrum 210 has two bands 212, 214, the second derivative spectrum 220 has three bands 222, 224, 226, the third derivative spectrum 230 has four bands 232, 234, 236, 238, and the fourth derivative spectrum 240 has five bands 242, 244, 246, 248, 250). The added complexity in the derivative spectrum can provide much useful information for the qualitative analysis of the material. Secondly, the derivative spectrum can resolve closely placed absorption bands which cannot be resolved in the absorbance mode. In the spectral curve 100 of FIG. 1A, the two components of the absorbance 102, 104 cannot be resolved from the absorption spectrum. However, from the fourth-order derivative spectrum 150 shown in FIG. 1B, the two absorption bands 152, 154 can be clearly visible. Thirdly, the derivation of the absorption spectrum can be used to discriminate absorbance bands with different bandwidths but same amplitude. The amplitude of an Nth order Gaussian band derivative spectrum is inversely proportional to the bandwidth of the original spectrum to the Nth degree. Therefore, the Nth-order derivative of a narrower spectrum has a larger amplitude than that of a broader spectrum.

Derivative spectra are mainly generated by optical or electrical methods. For optical methods, the frequency of the incident light is modulated with a narrow frequency (o by electromechanical methods, such as oscillating or rotating mirrors, or light source modulation to obtain first order and second order derivative spectrum. For dual wavelength methods, two spectrometers with a fixed center wavelength difference scan simultaneously to obtain a first-order derivative spectrum. Electrical methods use differential circuits consisting of analog resistance and capacitance devices to process a measured signal from a spectrometer readout to obtain the derivative data. However, both methods require high cost equipment and complex optics design, and such systems are typically very bulky. In addition, to estimate a derivative spectrum from an original absorption spectrum, a resolution of 2 nm or less is required for the original absorption spectrum. Many of existing spectrometers providing absorption spectra do not achieve such high resolution.

It is advantageous to have a spectrometer that provides an absorption spectrum having a resolution of 2 nm or less for further spectrum derivate estimation and that can be miniaturized in size, preferably implementable as an on-chip spectrometer. Based on this spectrometer and the high-resolution absorption spectrum that is obtained, a spectroscopy system for generating one or more derivative spectra is readily realizable in a small size. There is a need in the art to have such spectroscopy system.

SUMMARY OF THE INVENTION

An aspect of the present invention is to provide a derivative spectroscopy system for generating one or more derivative spectra of an input optical signal.

The system comprises a first dispersive-element structure for spectrally decomposing the input optical signal into plural subband signals. The first dispersive-element structure comprises one or more first dispersive elements. An individual first dispersive element may be realized as, for example, an AWG, an echelle grating or an etched diffraction grating.

The system further comprises a second dispersive-element structure for receiving one or more of the subband signals and spectrally decomposing the received one or more subband signals into a plurality of spectral components. The second dispersive-element structure comprises one or more second dispersive elements. An individual second dispersive element may be realized as, for example, an AWG, an echelle grating or an etched diffraction grating. An individual spectral component is narrower than an individual subband signal in spectral width. Advantageously, an optically transmissive material used to build the one or more second dispersive elements has a temperature-variant refractive index. The second dispersive-element structure is configured to utilize the temperature-variant refractive index to shift a center wavelength of the individual spectral component upon a change of a temperature of the second dispersive-element structure.

In the system, a heating structure is used to change the temperature of the second dispersive-element structure. Preferably, the heating structure comprises a temperature sensor for monitoring the temperature of the second dispersive-element structure and acting as a feedback control for the heating structure.

A plurality of optical detectors in the system is used for transducing the plurality of spectral components into a plurality of intensity signals.

The system further comprises one or more processors. The one or more processors are configured to estimate the one or more derivative spectra according to spectral-component sets each being the plurality of intensity signals obtained at one predetermined temperature of the second dispersive-element structure. Additionally, the one or more processors are further configured to control the heating structure to change the second dispersive-element structure to plural predetermined temperatures one by one for obtaining the spectral-component sets.

Preferably, the system further comprises an additional heating structure for changing a temperature of the first dispersive-element structure. The one or more processors are further configured to control the additional heating structure to maintain a temperature difference between the first- and second-dispersive-element structures to be within a value predetermined for reducing random disturbance in optical property of the first dispersive-element structure due to influx of heat from the second dispersive-element structure.

In one embodiment, the one or more subband signals received by the second dispersive-element structure exclude a fingerprint deficient spectrum of the input optical signal. This arrangement is useful in analyzing chemical or biological sample using near infrared absorption spectroscopy. Additionally, the system may be further configured such that the first dispersive-element structure is configured to process the input optical signal having a spectral range of 1150 nm to 1550 nm in wavelength, and the fingerprint deficient spectrum has a spectral range of 1250 nm to 1350 nm in wavelength.

To obtain first- and second-order derivative spectra of the input optical signal, the one or more processors may be further configured to estimate these derivative spectra according to three spectral-component sets obtained at three different predetermined temperatures of the second dispersive-element structure. Specifically, the one or more processors may be further configured as follows. First, control the heating structure to change the second dispersive-element structure to the predetermined temperatures $T_0$, $T_1$ and $T_2$ one by one for obtaining a first spectral-component set, a second one and a third one. The predetermined temperatures $T_0$, $T_1$ and $T_2$ are selected such that $\lambda_{T1}-\lambda_{T0}=\lambda_{T2}-\lambda_{T1}$ where $\lambda_{T0}$, $\lambda_{T1}$ and $\lambda_{T2}$ are center wavelengths of a same spectral component obtained at $T_0$, $T_1$ and $T_2$, respectively. Second, estimate values of the first- and second-order derivative spectra at $\lambda_{T0}$, respectively denoted as $I'_{T0}$ and $I''_{T0}$, by $I'_{T0}=(I_{T1}-I_{T0})/(\lambda_{T1}-\lambda_{T0})$ and $I''_{T0}=(I_{T0}+I_{T2}-2I_{T1})/(\lambda_{T1}-\lambda_{T0})^2$ where $I_{T0}$, $I_{T1}$ and $I_{T2}$ are values of the intensity signals of said same spectral component as recorded in the first, second and third spectral-component sets, respectively.

In realizing the system, one may integrate the first and second dispersive-element structures, the heating structure, the plurality of optical detectors, and optionally the additional heating structure to form an on-chip spectrometer.

Other aspects of the present invention are disclosed as illustrated by the embodiments hereinafter.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with the present invention.

FIGS. 1A and 1B both depict a typical situation that a total absorption spectrum has two absorbance bands with very close center wavelengths, where FIG. 1A depicts the total absorption spectrum and FIG. 1B depicts a fourth-order derivative of the total absorption spectrum.

FIG. 7B depicts, based on the original spectrum of FIG. 7, spectra with intensity signals obtained at temperatures $T_0$, $T_1$ and $T_2$ and a central wavelength $\lambda_{c,0}$ of each of the eight channels of the second dispersive-element structure of FIG.

4 for illustrating a shift of center wavelength of individual spectral component by heating the second dispersive-element structure.

Skilled artisans will appreciate that elements in the figures are illustrated for simplicity and clarity and have not necessarily been depicted to scale.

DETAILED DESCRIPTION

As used herein, a dispersive element means an optical device that disperses an input light beam composed of plural spectral components into a plurality of output light beams each having a portion of the spectral components, where the spectral-component portions of the output light beams are substantially non-overlapping.

The following detailed description is merely exemplary in nature and is not intended to limit the invention or the application and uses of the invention. Furthermore, there is no intention to be bound by any theory presented in the preceding background of the invention or the following detailed description.

It is the intent of the present disclosure to present a spectrometer based on photonic integrated circuits with a tunable dispersive-element structure such that the spectrometer is small and provides a tunable resolution of resolved spectral components as fine as 2 nm or even finer. Such high, tunable resolution enables computation of a derivative spectrum of an optical signal from the resolved spectral components with good accuracy. In one embodiment, an on-chip micro-spectrometer comprising two dispersive-element structures for spectrally decomposing an input optical signal to output spectral components covering a spectral range from 1150 nm to 1550 nm is described. The output spectral components are used for estimating one or more derivative spectra. In practical chemical and biological samples for sensing, not the whole spectral range is of interest in identifying chemicals in the samples. There is a fingerprint deficient spectrum within the spectral range of 1150 nm to 1550 nm where the fingerprint deficient spectrum is not useful for identification of chemical compounds. The use of the two dispersive-element structures enables discarding the fingerprint deficient spectrum within the spectral range for further processing, such that some reduction in implementation complexity is achievable.

In recent years, with the rapid development of integrated photonics, there has also been progress in the development of micro-spectrometers and their applications. Ultra-compact on-chip spectrometer systems based on photonic integrated circuits can achieve a fast processing rate with a small sample volume at low cost when mass-produced. The integrated micro-spectrometers can be realized in different configurations by using resonant wavelength filters, such as micro-ring resonators and Mach-Zender interferometers, and dispersive components like echelle gratings, etched diffraction gratings, and arrayed-waveguide gratings (AWGs). The AWGs have been widely used in wavelength-division multiplexing for optical communications, contributing to the development of highly scalable on-chip refractive index sensors and spectroscopy sensors based on AWGs.

The spectrometer as provided herein achieves a high, tunable spectral resolution by advantageously using a characteristic of an optically transmissive material used in forming a dispersive element. The material has a refractive index that varies by some external factors such as an application of an electric field, a magnetic field, a change in electron-hole concentration and a change of temperature. When such material is used to build certain dispersive elements including echelle gratings, etched diffraction gratings and AWGs, a change of refractive index in the material can be used to generate a minute change of dispersion characteristics of these dispersive elements. The inventors advantageously utilize a change of temperature of a dispersive element realized by such material having temperature-variant refractive index to give a small, tunable shift in center wavelengths of spectral components resolved by the dispersive element. This small shift is as low as 2 nm or lower, enabling the spectrometer provided herein to provide a high, tunable spectral resolution of resolved spectral components to be used for computing derivative spectra.

An aspect of the present invention is to provide a derivative spectroscopy system for generating one or more derivative spectra of an input optical signal. The system is realizable as an on-chip spectrometer. The system may also be realized into multiple chips packaged together to form a resultant spectrometer. Alternatively, in the system, computation of the one or more derivative spectra from measured spectral components of the input optical signal may be delegated to a standalone processor or a computer while an on-chip spectrometer, which mainly contains optical components and electrical circuit elements, is fabricated for generating the spectral components from the input optical signal. The on-chip spectrometer may also be implemented with a wireless communication circuit for wirelessly transmitting the measured spectral components to the computer.

Figure 3:
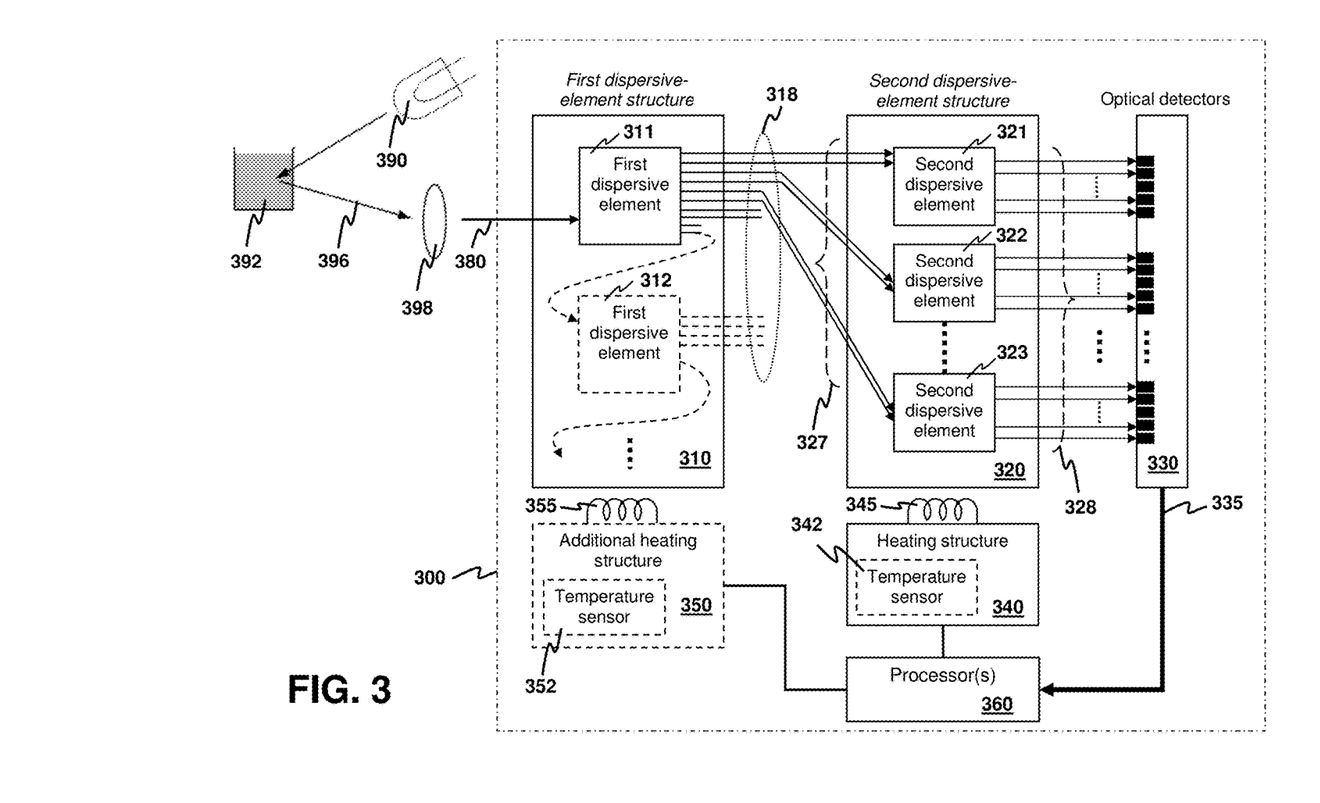
FIG. 3 depicts a schematic diagram of a system for derivative spectroscopy in accordance with an exemplary embodiment of the present invention, where the system employs first and second dispersive-element structures for decomposing an input optical signal into a plurality of output spectral components.

An exemplary embodiment of the system in accordance with the present invention is depicted in FIG. 3. A derivative spectroscopy system 300 receives an input optical signal 380 for generating one or more derivative spectra. The system 300 comprises a first dispersive-element structure 310, a second dispersive-element structure 320, a heating structure 340, a plurality of optical detectors 330, and one or more processors 360.

The first dispersive-element structure 310 is used for spectrally decomposing the input optical signal 380 into plural subband signals 318. Each of the subband signals 318 has a center wavelength and a spectral width. The first dispersive-element structure 310 comprises one or more first dispersive elements (represented in FIG. 3 by a leading first dispersive element 311 and an optional first dispersive element 312). Examples of an individual first dispersive element include an AWG, an echelle grating and an etched diffraction grating. The first dispersive-element structure 310 receives the input optical signal 380 by feeding the input optical signal 380 to the leading first dispersive element 311. If the system 300 is intended for analyzing the input optical signal 380 that is known to contain a fingerprint deficient spectrum not useful for chemical composition determination as mentioned above, some of the subband signals 318 located in the fingerprint deficient spectrum may be discarded.

In the system 300, one or more of the subband signals 318 are selected to form an input or inputs 327 to the second dispersive-element structure 320. It is possible that all the subband signals 318 are selected. The second dispersive-element structure 320 is used for spectrally decomposing said input or inputs 327 into a plurality of spectral components 328. Each of the spectral components 328 has a center wavelength and a spectral width. An individual spectral component is narrower than an individual subband signal in spectral width. The second dispersive-element structure 320 is formed by including one or more second dispersive elements (represented in FIG. 3 by second dispersive elements 321, 322, 323). Examples of an individual second dispersive element include an AWG, an echelle grating and an etched diffraction grating. The one or more second dispersive elements 321, 322, 323 and the one or more first dispersive elements 311, 312 may or may not be realized with the same type of dispersive element. The plurality of spectral components 328 is sensed and converted to a plurality of intensity signals 335 by the plurality of optical detectors 330. The plurality of intensity signals 335 is readable by the one or more processors 360.

One main feature of the second dispersive-element structure 320 is that an optically transmissive material used to build the one or more second dispersive elements 321, 322, 323 has a temperature-variant refractive index. The temperature-variant refractive index is advantageously utilized by the second dispersive-element structure 320 to create a shift of the center wavelength of the individual spectral component upon a change of a temperature of the second dispersive-element structure 320.

The heating structure 340, comprising one or more heating elements (represented by a first coil 345 in FIG. 3), is used for changing the temperature of the second dispersive-element structure 320. In an integrated circuit implementation of the system 300, the one or more heating elements 345 are usually implemented as one or more resistors located adjacent to the one or more second dispersive elements 321, 322, 323. Preferably, the heating structure 340 further comprises a temperature sensor 342 for monitoring the temperature of the second dispersive-element structure 320 and acting as a feedback control for the heating structure 340.

The system 300 is desired to generate the one or more derivative spectra of the input optical signal 380. The one or more processors 360 are configured to estimate the one or more derivative spectra according to plural spectral-component sets, where each of the spectral-component sets is the plurality of intensity signals 335 obtained at one predetermined temperature of the second dispersive-element structure 320. The one or more processors 360 are further configured to change the second dispersive-element structure 320 to plural predetermined temperatures one by one for obtaining the spectral-component sets. Further elaboration on obtaining the spectral-component sets and estimating the one or more derivative spectra will be provided in various embodiments and illustrative examples hereinafter.

It is not desirable that heating the second dispersive-element structure 320 affects operation of the first dispersive-element structure 310. However, a temperature difference between the first and second dispersive-element structures 310, 320 creates a flow of heat from the second dispersive-element structure 320 to the first dispersive-element structure 310. Since the second dispersive-element structure 320 is required to reach different temperatures from time to time, it is possible that the flow of heat in turn creates a temperature gradient across the first dispersive-element structure 310 where the temperature gradient varies from time to time, causing random disturbance to optical property of the first dispersive-element structure 310 (such as change of refractive index in the one or more first dispersive elements 311, 312). Although an ideal solution is to prevent heat flowing from the second dispersive-element structure 320 to the first dispersive-element structure 310, fabricating a thermal-insulation barrier between the two structures 310, 320 is not compatible with commonly-used integrated circuit manufacturing processes. To reduce the random disturbance to optical property, one may reduce a temperature difference between the two structures 310, 320 so as to reduce an influx of heat from the second dispersive-element structure 320 to the first dispersive-element structure 310. In one embodiment, an additional heating structure 350, comprising one or more second heating elements (represented by a second coil 355 in FIG. 3), is introduced to the system 300 for changing a temperature of the first dispersive-element structure 310. Similar to the heating structure 340, the one or more second heating elements 355 may be implemented as one or more resistors located adjacent to the one or more first dispersive elements 311, 312. Preferably, the additional heating structure 350 further comprises a second temperature sensor 352 to monitor a temperature of the first dispersive-element structure 310. The one or more processors 360 are further configured to control the additional heating structure 350 to maintain the temperature difference between the first- and second dispersive-element structures 310, 320 to be within a certain value. This value is predetermined for reducing the aforesaid random disturbance in optical property of the first dispersive-element structure 310 due to influx of heat from the second dispersive-element structure 320.

The system 300 is usually used to determine a chemical composition of a sample 392 by absorption spectroscopy. In operation, one may use a light source 390 to shine a probe light beam on the sample 392. The light source 390 is generally a broadband light source having an emission spectrum covering a spectrum of interest used in measuring the sample 392. Reflected optical signal 396 may be focused by ancillary optics 398, such as a lens, to form the input optical signal 380. The system 300 processes the input optical signal 380 to yield the one or more derivative spectra such as a second-order derivative spectrum. Based on the one or more derivative spectra that are generated by the system 300, those skilled in the art may determine the chemicals present in the sample 392. Note that heating the second dispersive-element structure 320 to each predetermined temperature takes time. Therefore, the sample 392 needs to be chemically stable at least over the total duration of time that heating takes place.

Figure 4:
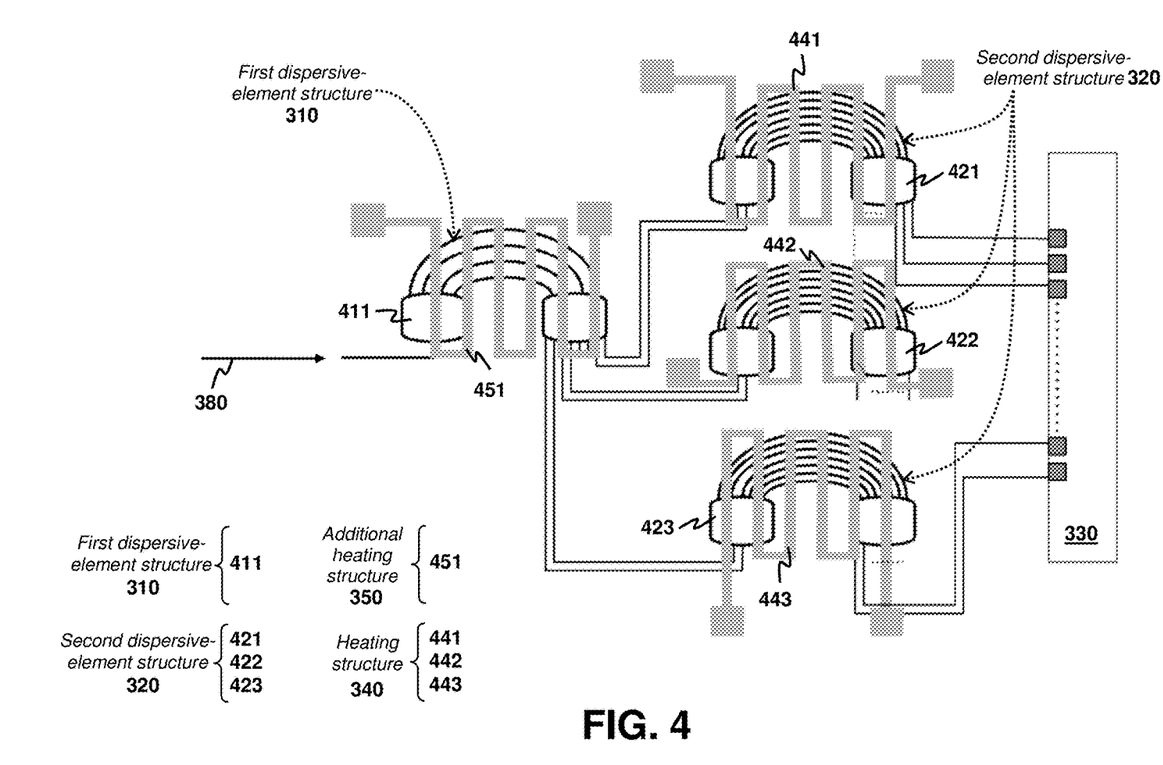
FIG. 4 depicts one realization of the first and second dispersive-element structures of the system of FIG. 3, where each dispersive element in these two structures is implemented as an AWG.

FIG. 4 depicts one practical realization and arrangement of the first and second dispersive-element structures 310, 320 realized by AWGs with placement of the heating structure 340 and the additional heating structure 350. The first dispersive-element structure 310 has a first-stage AWG 411 as the only one first dispersive element (acting as the leading first dispersive element 311). The second dispersive-element structure 320 has three second-stage AWGs 421, 422, 423. The heating structure 340 comprises three heaters 441, 442, 443. The heaters 441, 442, 443 are directly positioned on and are in close proximity to the three second-stage AWGs 421, 422, 423 of the second dispersive-element structure 320, respectively, enabling the heating structure 340 to uniformly heat the three second-stage AWGs 421, 422, 423 for an advantage that the second dispersive-element structure 320 reaches a target temperature with a negligible temperature variation among the three second-stage AWGs 421, 422, 423. For a similar advantage, a heater 451 of the additional heating structure 350 is positioned on the first-stage AWG 411. Typically, each of the heaters 441, 442, 443, 451 is implemented as a resistor for a manufacturing advantage of simple implementation on an on-chip spectrometer. Applying a current to the resistor generates heat. Although all the heaters 441, 442, 443, 451 mentioned above are shown in FIG. 4 to be positioned on their respective first- or second-stage AWGs in order to keep in close proximity thereto, other positional arrangements of the heaters 441, 442, 443, 451 for keeping close proximity to their respective first- or second-stage AWGs are also possible, such as putting the heaters 441, 442, 443, 451 around their respective first- or second-stage AWGs.

Figure 5:
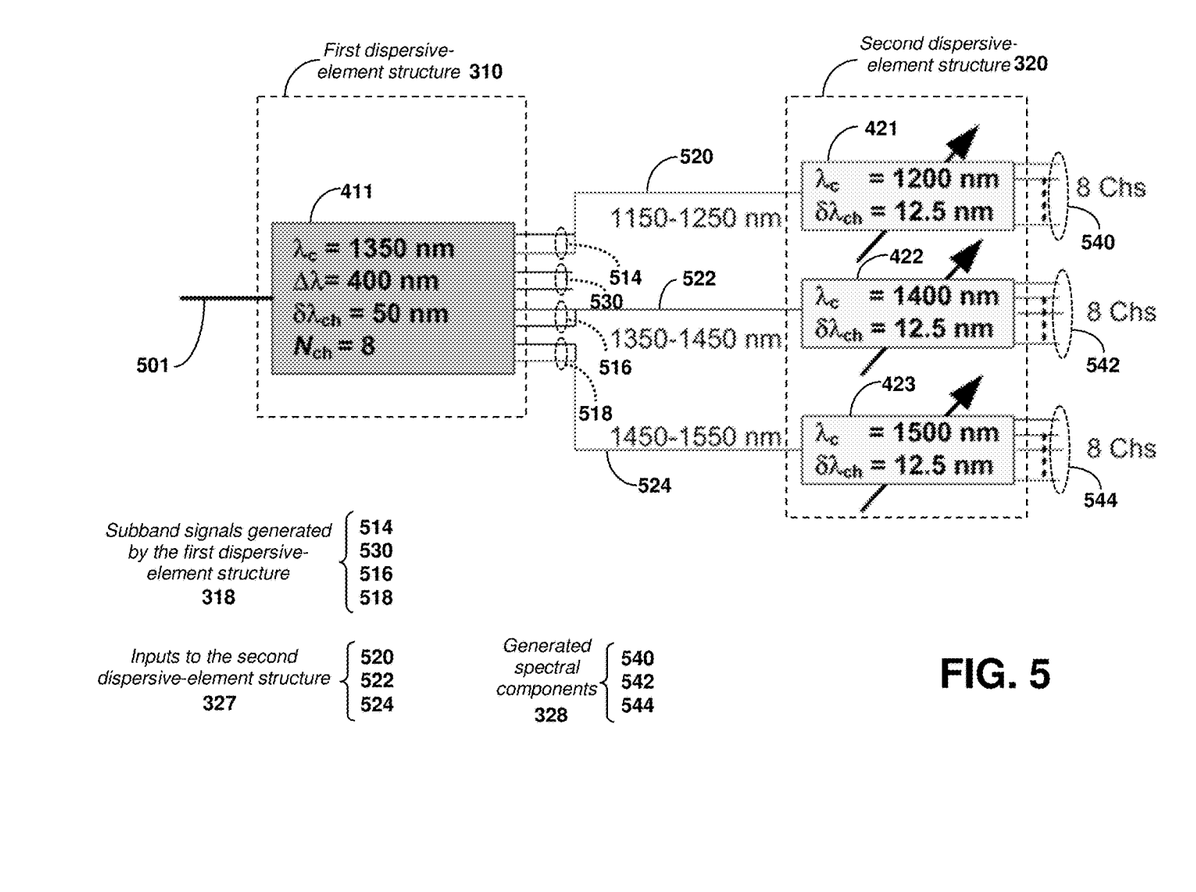
FIG. 5 illustrates a two-stage spectral decomposition of an input optical signal for chemical or biological sensing by the first and second dispersive-element structures of FIG. 4.
Figure 6:
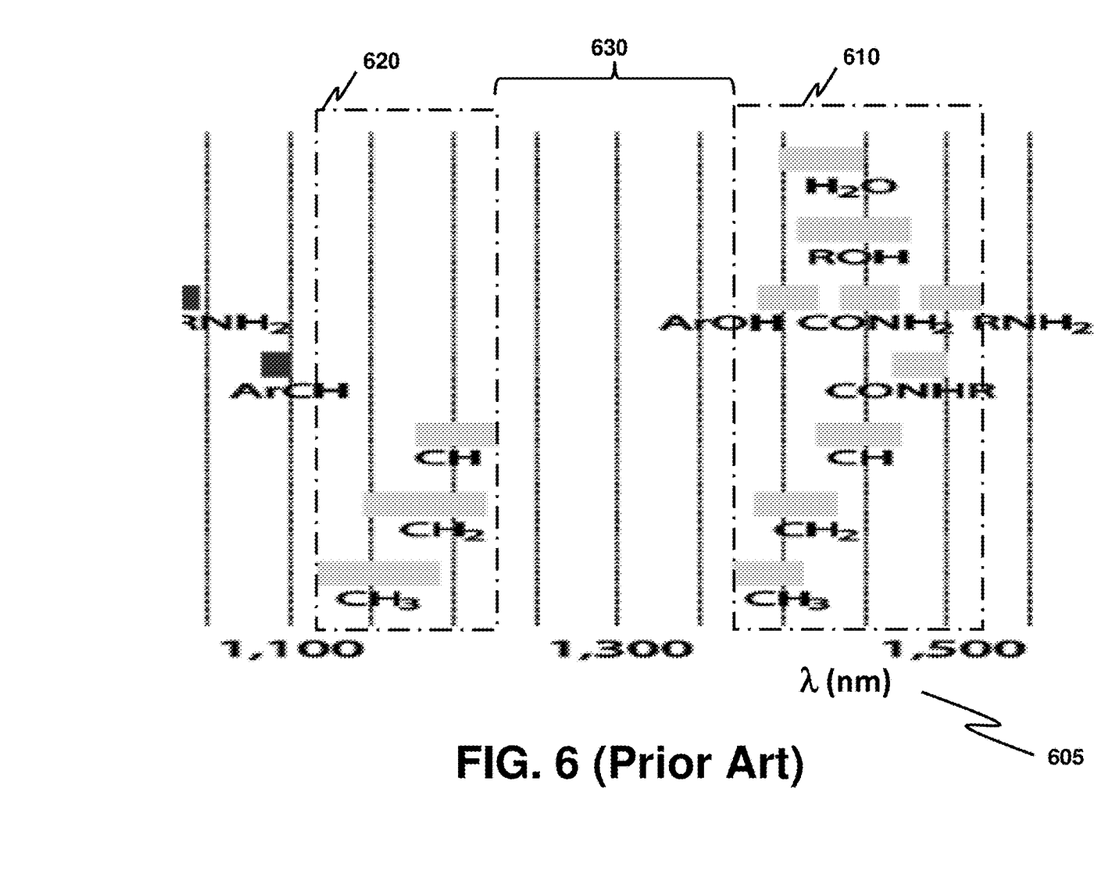
FIG. 6 depicts a graph showing absorption regions of different chemicals, where a first overtone region, a second overtone region, and a fingerprint deficient region between the first and second overtone regions are identified in the absorption regions.

In one application for analyzing chemical or biological samples, the system 300 with the first and second dispersive-element structures 310, 320 realized by AWGs according to FIG. 4 is used to analyze the sample 392 by near infrared (NIR) absorption spectroscopy with a spectrum of interest in the range of 1150 nm to 1550 nm excluding a fingerprint deficient spectrum of 1250 nm to 1350 nm. FIG. 6, which plots absorption regions in wavelength λ 605 for different chemical bonds, briefly explains the occurrence of fingerprint deficient spectrum. Optical absorption of a chemical bond occurs at frequencies that are overtones of a certain fundamental frequency (or wavelength). Also, overtone frequencies of many chemical bonds, such as CH, $CH_2$ and $CH_3$, are close together, forming clustered regions of interest such as a first overtone region 610 and a second overtone region 620. Between the first and second overtone regions 610, 620, a lacking of optical absorption for many chemical bonds gives rise to a fingerprint deficient spectrum 630. FIG. 5 depicts an arrangement of spectral decomposition provided by the first-stage AWG 411 and the three second-stage AWGs 421, 422, 423 for the aforesaid application. Each of the first-stage AWG 411 and the three second-stage AWGs 421, 422, 423 is a one-input eight-output AWG.

The first-stage AWG 411 is configured to receive an optical input 501 having a center wavelength $\lambda_c$ of 1350 nm and a spectral width $\Delta\lambda$ of 400 nm. The optical input 501 is the input optical signal 380. The first-stage AWG 411 disperses the optical input 501 to eight output channels each having a spectral width $\delta\lambda_{ch}$ of 50 nm.

The two output channels 514 of the first-stage AWG 411, collectively providing a subband signal in the range of 1150 nm to 1250 nm, are aggregated together to provide an input 520 to the second-stage AWG 421. This second-stage AWG 421 is configured to process the input 520 with a center wavelength $\lambda_c$ of 1200 nm and to have each output channel a spectral width $\delta\lambda_{ch}$ of 12.5 nm. This second-stage AWG 421 generates spectral components of the input optical signal 380 at a first group of eight output channels 540.

The next two output channels 530 of the first-stage AWG 411 falls into the fingerprint deficient spectrum of 1250 nm to 1350 nm, and are discarded. Thus, implementation of the second dispersive-element structure 320 is simplified by eliminating an additional second-stage AWG to process the subband signal of the two output channels 530.

The subsequent two output channels 516 of the first-stage AWG 411 are aggregated together to provide a resultant subband signal in the range of 1350 nm to 1450 nm. This resultant subband signal is provided to an input 522 of the second-stage AWG 422. This second-stage AWG 422 is configured to process the input 522 with a center wavelength $\lambda_c$ of 1400 nm and to have each output channel a spectral width $\delta\lambda_{ch}$ of 12.5 nm, thereby generating spectral components of the input optical signal 380 at a second group of eight output channels 542.

Similarly, the last two output channels 518 of the first-stage AWG 411 collectively provide a resultant subband signal in the range of 1450 nm to 1550 nm, and are aggregated together to provide an input 524 of the second-stage AWG 423. This second-stage AWG 423 is configured to process the input 524 with a center wavelength $\lambda_c$ of 1500 nm and to have each output channel a spectral width $\delta\lambda_{ch}$ of 12.5 nm, thereby generating spectral components of the input optical signal 380 at a third group of eight output channels 544.

The spectral components 328 obtained at the three output-channel groups 540, 542, 544 are processed by the plurality of optical detectors 330 to detect a signal intensity I of each of the spectral components 328.

Figure 7A:
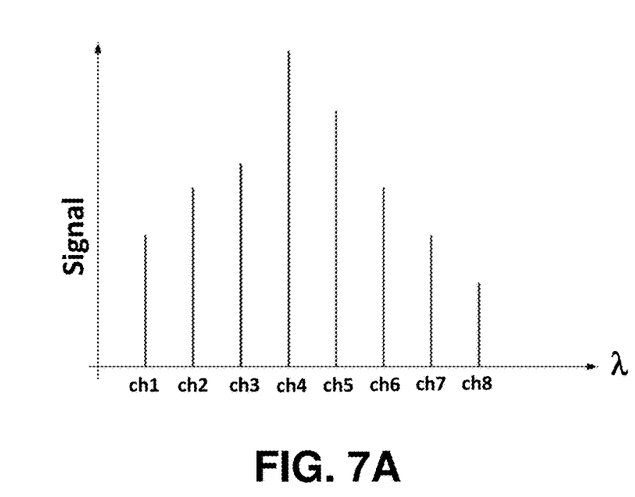
FIG. 7A depicts an illustrative example of an original spectrum with intensity signal at temperature $T_0$ and a central wavelength $\lambda_{c,0}$ of each of the eight output spectral components of the second dispersive-element structure of FIG. 4.
Figure 7B:
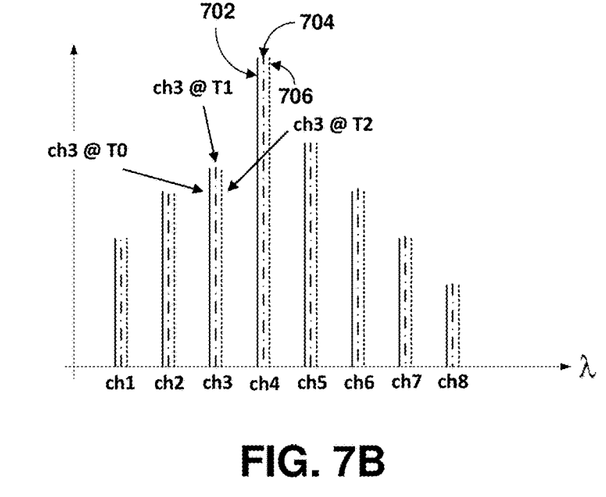

FIGS. 7A and 7B illustrate generation of the spectral-component sets that are subsequently used for estimating the one or more derivative spectra. FIG. 7A depicts an original spectrum showing intensity signals obtained at temperature $T_0$ and a central wavelength, denoted as $\lambda_{c,0}$, of each of the eight output channels of an individual AWG selected from the three second-stage AWGs 421, 422, 423. A spectrum derivative is determined by the subtraction of the spectra at different temperatures $T_0$, $T_1$ and $T_2$ based on the following relationship of an AWG with center wavelength $\lambda_c$:

$$\lambda_c = (n_a/m)\Delta L \qquad (4)$$

where $n_a$ is an effective index of waveguide mode of a second-stage AWG, m is the diffraction order and $\Delta L$ is the length difference of the waveguide gratings. An effective index is used to describe the propagation behavior of electromagnetic wave inside a confined structure. The effective index $n_a$ is related to the waveguide structure (geometry) of the second-stage AWG and the refractive index of the optically transmissive material used in building the second-stage AWG. For the system 300 described in the present embodiment, the structure of each of the three second-stage AWGs 421, 422, 423 is assumed to be invariant so that a change in refractive index of the optically transmissive material by heating leads to a change of the effective index $n_a$ and then a shift of center wavelength. For details, see M. K. Smit and C. Van Dam, "PHASAR-based WDM-devices: Principles, design and applications," *IEEE Journal of Selected Topics in Quantum Electronics*, vol. 2, issue 2, pp. 236-250, June 1996.

In order to generate spectrum derivatives, heating the three second-stage AWGs 421, 422, 423 is used to tune the wavelength of each output channel simultaneously. When a current is applied to the heating structure 340, a change of the temperature of the three second-stage AWGs 421, 422, 423 produces a change of the effective index $n_a$ of the three second-stage AWGs 421, 422, 423, thereby shifting the center wavelength $\lambda_{c,0}$.

As an example illustrated in FIG. 7B, the center wavelength 702 at one of the three second-stage AWGs 421, 422, 423 is shifted to $\lambda_{c,1}$ 704 and $\lambda_{c,2}$ 706 at temperatures $T_1$ and $T_2$, respectively. The wavelength difference is around two nanometers, i.e. $|\lambda_{c,0} - \lambda_{c,1}| \le 2$ nm. The spectra at temperatures $T_0$, $T_1$ and $T_2$ are recorded. The first- and second-order derivative spectra can then be calculated by the one or more processors 360 based on the spectral-component sets captured at the three temperature values. The temperatures $T_0$, $T_1$ and $T_2$ are dependent on the waveguide structure and material; for example, $T_0$, $T_1$ and $T_2$ can be 300K, 350K and 400K, respectively.

Although heating is used as a means for creating a refractive index change in illustrating the present embodiment, the change of refractive index may be effected by other means in other embodiments of the present invention. The center wavelength of the second dispersive-element structure 320 may be configured by applying one of an electric field, a magnetic field, a change in electron-hole concentration or heating to the three second-stage AWGs 421, 422, 423 to create a refractive index change in order to shift the center wavelength of each of the spectral components 328.

Figure 8:
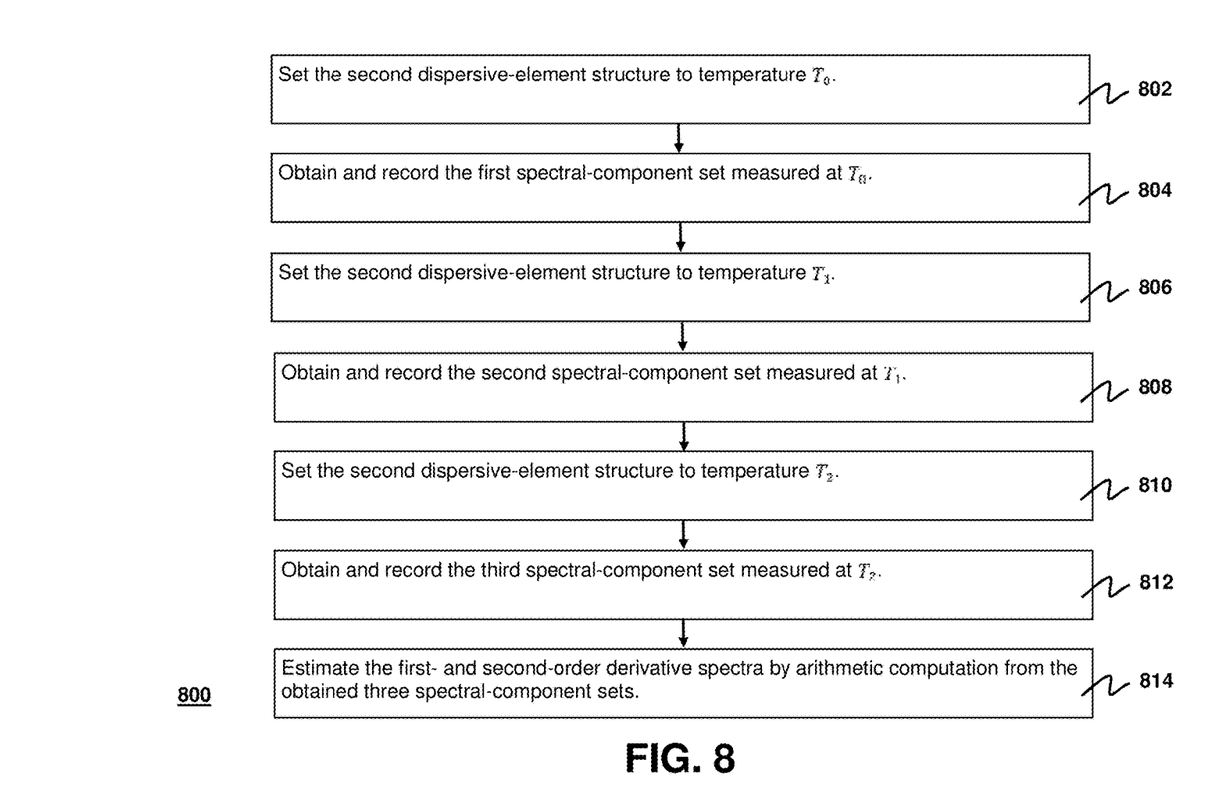
FIG. 8 depicts a flowchart of operation of the system of FIG. 3 for estimating first- and second-order derivative spectra in accordance with one embodiment of the present invention.

FIG. 8 is a flowchart 800 illustrating the steps of estimating the first- and second-order derivative spectra based on spectral-component sets captured at three temperatures in accordance with one embodiment of the present invention. Three spectral-component sets are first obtained at three different temperatures of the second dispersive-element structure 320. The first- and second-order derivative spectra are then estimated based on the three obtained spectral-component sets.

In a step 802, the one or more processors 360 control the heating structure 340 to set the temperature of the second dispersive-element structure 320 to a first predetermined temperature $T_0$. After the temperature $T_0$ is reached, the one or more processors 360 receive the plurality of intensity signals 335 from the plurality of optical detectors 330, the received plurality of intensity signals 335 being recorded as a first spectral-component set (step 804).

In a step 806, the one or more processors 360 control the heating structure 340 to change the temperature of the second dispersive-element structure 320 from $T_0$ to a second predetermined temperature $T_1$. After the temperature $T_1$ is reached, the one or more processors 360 receive the plurality of intensity signals 335 again from the plurality of optical detectors 330, where the received plurality of intensity signals 335 is recorded as a second spectral-component set (step 808).

In a step 810, the one or more processor 360 control the heating structure 340 to change the temperature of the second dispersive-element structure 320 from $T_1$ to a third predetermined temperature $T_2$. After the temperature $T_2$ is reached, the one or more processors 360 receive the plurality of intensity signals 335 one more time from the plurality of optical detectors 330, where the received plurality of intensity signals 335 is recorded as a third spectral-component set (step 812).

In the steps 802, 806 and 810, the three predetermined temperatures $T_0$, $T_1$ and $T_2$ are selected such that $\lambda_{T1}-\lambda_{T0}=\lambda_{T2}-\lambda_{T1}$ where $\lambda_{T0}$, $\lambda_{T1}$ and $\lambda_{T2}$ are center wavelengths of a same spectral component obtained at $T_0$, $T_1$ and $T_2$, respectively. That is, an equal shift in center wavelength, denoted as $\Delta\lambda$, is obtained for the temperature changed from $T_0$ to $T_1$ and from $T_1$ to $T_2$. As mentioned above, it is desirable to have $\Delta\lambda \leq 2$ nm.

In a step 814, the first- and second-order derivative spectra are estimated by arithmetic computation from the obtained three spectral-component sets. Each of the three spectral-component sets contains intensity signals for the plurality of spectral components 328. In the three spectral-component sets, one is able to identify three intensity values, each from one of the sets, belonging to a same spectral component. As an example for illustration, this same spectral component may be the first output channel in the first group of eight output channels 540. Without loss of generality, denote $I_{T0}$, $I_{T1}$ and $I_{T2}$ as values of the intensity signals of a certain same spectral component as recorded in the first, second and third spectral-component sets, respectively. Furthermore, this same spectral component has center wavelengths $\lambda_{T0}$, $\lambda_{T1}$ and $\lambda_{T2}$ at $T_0$, $T_1$ and $T_2$, respectively. Also denote values of first- and second-order derivative spectra at $\lambda_{T0}$ as $I'_{T0}$ and $I''_{T0}$, respectively. Similarly, denote $I'_{T1}$ as a value of first-order derivative spectra at $\lambda_{T1}$. According to the finite difference method in Mathematics, $I'_{T0}$, $I'_{T1}$ and $I''_{T0}$ are given by $$I'_{T0} = \frac{I_{T1} - I_{T0}}{\lambda_{T1} - \lambda_{T0}}, \quad (5)$$

$$I'_{T1} = \frac{I_{T2} - I_{T1}}{\lambda_{T2} - \lambda_{T1}}, \text{ and} \quad (6)$$

$$I''_{T0} = \frac{I'_{T1} - I'_{T0}}{\frac{\lambda_{T2} - \lambda_{T0}}{2}}. \quad (7)$$

Since $\Delta\lambda = \lambda_{T2} - \lambda_{T1} = \lambda_{T1} - \lambda_{T0}$, it follows that $I''_{T0}$ given by (7) is reduced to $$I''_{T0} = \frac{I_{T0} + I_{T2} - 2I_{T1}}{(\Delta\lambda)^2}. \quad (8)$$

Thus, it can be seen that the present embodiment provides a method, a system and an apparatus for derivative spectroscopy with estimation of the first- and second-order derivative spectra based on three spectral-component sets captured at three temperature values.

Those skilled in the art will appreciate that the procedure detailed according to the flowchart 800 is extensible for estimating higher-order derivative spectra of the input optical signal 380. In particular, an mth-order derivative spectrum is estimable by using m+1 spectral-component sets obtained at m+1 temperatures.

In one implementation of the system 300, the first and second dispersive-element structures 310, 320, the heating structure 340, the plurality of optical detectors 330 and optionally the additional heating structure 350 may be integrated together to form an on-chip spectrometer. It is also possible to further integrate the one or more processors 360 into the on-chip spectrometer. In some situations, however, the computation of the one or more derivative spectra from the obtained spectral-component sets may be better handled by a standalone processor (e.g., a high-speed processor) or a computer (due to, e.g., provision of a user interface). In these situations, it may not be preferable to integrate the one or more processors 360 into the on-chip spectrometer. Yet in some situations, the one or more processors 360 are implemented with multiple processors, some of which are dedicated to controlling the heating structure 340 and/or the additional heating structure 350, the others of which are used for computing the one or more derivative spectra. In implementation of the system 300, one may integrate the processor(s) dedicated to controlling on-chip components into the on-chip spectrometer.

While exemplary embodiments have been presented in the foregoing detailed description of the invention, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of steps and method of operation described in the exemplary embodiment without departing from the scope of the invention as set forth in the appended claims.

What is claimed is:

1. A derivative spectroscopy system for generating one or more derivative spectra of an input optical signal comprising:
    a first dispersive-element structure for spectrally decomposing the input optical signal into plural subband signals, the first dispersive-element structure comprising one or more first dispersive elements;
    a second dispersive-element structure for receiving one or more of the subband signals and spectrally decomposing the received one or more subband signals into a plurality of spectral components, the second dispersive-element structure comprising one or more second dispersive elements, an individual spectral component being narrower than an individual subband signal in spectral width, the individual spectral component having a center wavelength, wherein an optically transmissive material used to build the one or more second dispersive elements has a temperature-variant refractive index, and the second dispersive-element structure is configured to utilize the temperature-variant refractive index to shift the center wavelength of the individual spectral component upon a change of a temperature of the second dispersive-element structure;
    a heating structure for changing the temperature of the second dispersive-element structure;
    a plurality of optical detectors for transducing the plurality of spectral components into a plurality of intensity signals; and
    one or more processors configured to:
        estimate the one or more derivative spectra according to spectral-component sets each being the plurality of intensity signals obtained at one predetermined temperature of the second dispersive-element structure; and
        control the heating structure to change the second dispersive-element structure to plural predetermined temperatures one by one for obtaining the spectral-component sets.

2. The derivative spectroscopy system of claim 1, wherein the second dispersive element is an array-waveguide grating (AWG).

3. The dispersive spectroscopy system of claim 1, wherein the second dispersive element is an echelle grating.

4. The dispersive spectroscopy system of claim 1, wherein the second dispersive element is an etched diffraction grating.

5. The derivative spectroscopy system of claim 1, wherein the heating structure comprises a temperature sensor for monitoring the temperature of the second dispersive-element structure and acting as a feedback control for the heating structure.

6. The derivative spectroscopy system of claim 1 further comprising:
    an additional heating structure for changing a temperature of the first dispersive-element structure;
    wherein the one or more processors are further configured to control the additional heating structure to maintain a temperature difference between the first- and second dispersive-element structures to be within a value predetermined for reducing random disturbance in optical property of the first dispersive-element structure due to influx of heat from the second dispersive-element structure.

7. The derivative spectroscopy system of claim 1, wherein the one or more subband signals received by the second dispersive-element structure exclude a fingerprint deficient spectrum of the input optical signal.

8. The derivative spectroscopy system of claim 7, wherein:
    the first dispersive-element structure is configured to process the input optical signal having a spectral range of 1150 nm to 1550 nm in wavelength; and
    the fingerprint deficient spectrum has a spectral range of 1250 nm to 1350 nm in wavelength.

9. The derivative spectroscopy system of claim 1, wherein the one or more processors are further configured to estimate a first-order derivative spectrum and a second-order derivative spectrum of the input optical signal according to three spectral-component sets obtained at three different predetermined temperatures of the second dispersive-element structure.

10. The derivative spectroscopy system of claim 1, wherein the one or more derivative spectra include a first-order derivative spectrum and a second-order derivative spectrum, and wherein the one or more processors are further configured to:
    control the heating structure to change the second dispersive-element structure to the predetermined temperatures $T_0$, $T_1$ and $T_2$ one by one for obtaining first, second and third spectral-component sets, wherein $T_0$, $T_1$ and $T_2$ are selected such that $\lambda_{T1}-\lambda_{T0}=\lambda_{T2}-\lambda_{T1}$ where $\lambda_{T0}$, $\lambda_{T1}$ and $\lambda_{T2}$ are center wavelengths of a same spectral component obtained at $T_0$, $T_1$ and $T_2$, respectively; and
    estimate values of the first- and second-order derivative spectra at $\lambda_{T0}$, respectively denoted as $I'_{T0}$ and $I''_{T0}$, by $$I'_{T0} = \frac{I_{T1} - I_{T0}}{\lambda_{T1} - \lambda_{T0}} \text{ and } I''_{T0} = \frac{I_{T0} + I_{T2} - 2I_{T1}}{(\lambda_{T1} - \lambda_{T0})^2}$$

where $I_{T0}$, $I_{T1}$ and $I_{T2}$ are values of the intensity signals of said same spectral component as recorded in the first, second and third spectral-component sets, respectively.

11. The derivative spectroscopy system of claim 1, wherein the first dispersive-element structure consists of a single first dispersive element.

12. The derivative spectroscopy system of claim 1, wherein the first and second dispersive-element structures, the heating structure and the plurality of optical detectors are integrated to form an on-chip spectrometer.

13. The derivative spectroscopy system of claim 2, wherein the first and second dispersive-element structures, the heating structure and the plurality of optical detectors are integrated to form an on-chip spectrometer.

14. The derivative spectroscopy system of claim 3, wherein the first and second dispersive-element structures, the heating structure and the plurality of optical detectors are integrated to form an on-chip spectrometer.

15. The derivative spectroscopy system of claim 4, wherein the first and second dispersive-element structures, the heating structure and the plurality of optical detectors are integrated to form an on-chip spectrometer.

16. The derivative spectroscopy system of claim 5, wherein the first and second dispersive-element structures, the heating structure and the plurality of optical detectors are integrated to form an on-chip spectrometer.

17. The derivative spectroscopy system of claim 6, wherein the first and second dispersive-element structures, the heating structure, the additional heating structure and the plurality of optical detectors are integrated to form an on-chip spectrometer.

18. The derivative spectroscopy system of claim 7, wherein the first and second dispersive-element structures, the heating structure and the plurality of optical detectors are integrated to form an on-chip spectrometer.

19. The derivative spectroscopy system of claim 8, wherein the first and second dispersive-element structures, the heating structure and the plurality of optical detectors are integrated to form an on-chip spectrometer.

20. The derivative spectroscopy system of claim 10, wherein the first and second dispersive-element structures, the heating structure and the plurality of optical detectors are integrated to form an on-chip spectrometer.

* * * * *